United States Patent
Sluggett et al.

(10) Patent No.: US 11,040,136 B2
(45) Date of Patent: Jun. 22, 2021

(54) INFUSION DEVICE

(71) Applicant: Infusion Innovations Pty Ltd, South Australia (AU)

(72) Inventors: Andrew Sluggett, South Australia (AU); Danny Djurasevich, South Australia (AU); Paul Crockett, South Australia (AU); Gabriel Ash, South Australia (AU)

(73) Assignee: Infusion Innovations Pty Ltd, South Australian (AU)

( * ) Notice: Subject to any disclaimer, the term of this patent is extended or adjusted under 35 U.S.C. 154(b) by 0 days.

(21) Appl. No.: 16/034,301

(22) Filed: Jul. 12, 2018

(65) Prior Publication Data

US 2018/0318497 A1    Nov. 8, 2018

Related U.S. Application Data

(63) Continuation of application No. PCT/AU2017/050019, filed on Jan. 12, 2017.

(30) Foreign Application Priority Data

Jan. 12, 2016 (AU) ................................ 2016900078

(51) Int. Cl.
*A61M 5/142* (2006.01)
*G05B 15/00* (2006.01)
(Continued)

(52) U.S. Cl.
CPC .... *A61M 5/14228* (2013.01); *A61M 5/14244* (2013.01); *A61M 5/14586* (2013.01);
(Continued)

(58) Field of Classification Search
CPC .......... A61M 5/14228; A61M 5/14586; A61M 5/16831; A61M 2005/16863;
(Continued)

(56) References Cited

U.S. PATENT DOCUMENTS 4,191,181 A * 3/1980 Franetzki .......... A61M 5/14276
128/DIG. 12
4,624,661 A * 11/1986 Arimond .............. A61M 5/172
128/DIG. 12
(Continued)

FOREIGN PATENT DOCUMENTS

WO    WO 99/21596 A1    5/1999
WO    WO 02/066101 A2   8/2002
WO    WO 2013/102747 A2 7/2013

OTHER PUBLICATIONS

May 11, 2017 Search Report issued in International Application No. PCT/AU2017/050019.
(Continued)

*Primary Examiner* — Theodore J Stigell
(74) *Attorney, Agent, or Firm* — Edwin A. Sisson, Attorney at Law, LLC; Jeffrey J. Banyas

(57) ABSTRACT

Some embodiments are directed to portable devices for transferring fluids from an external source and controllably infusing the fluids into a patient, particularly portable infusion pump devices, and protective housings for such devices, which include a pump unit, a computer, a portable fuel source, and a seal for securing the contents substantially within the protective housings of the device. Some embodiments may be formed as a single infusion pump unit or may be formed when two infusion pump units are engaged. Some embodiments also relate to methods of use of portable devices and method for the manufacture of portable devices and protective housings for such devices.

16 Claims, 10 Drawing Sheets

(51) Int. Cl.
*G16H 20/17* (2018.01)
*A61M 5/145* (2006.01)
*A61M 5/168* (2006.01)
*G06F 12/14* (2006.01)
*A61M 5/14* (2006.01)

(52) U.S. Cl.
CPC ......... *A61M 5/16831* (2013.01); *G05B 15/00* (2013.01); *G06F 12/14* (2013.01); *G16H 20/17* (2018.01); *A61M 5/14212* (2013.01); *A61M 2005/1402* (2013.01); *A61M 2005/14208* (2013.01); *A61M 2005/14264* (2013.01); *A61M 2005/14506* (2013.01); *A61M 2005/16863* (2013.01); *A61M 2205/0216* (2013.01); *A61M 2205/52* (2013.01); *A61M 2205/584* (2013.01); *A61M 2205/587* (2013.01); *A61M 2205/82* (2013.01); *A61M 2205/8206* (2013.01); *A61M 2205/8268* (2013.01); *A61M 2207/00* (2013.01); *G06F 2212/1052* (2013.01)

(58) Field of Classification Search
CPC ........... A61M 2005/1402; A61M 2005/14264; A61M 2005/1416; A61M 5/14244; A61M 5/14212; A61M 2005/14208; A61M 2005/14506; A61M 2205/82; G06F 12/14; G16H 20/17; G05B 15/00
See application file for complete search history.

(56) References Cited

U.S. PATENT DOCUMENTS

| | | | |
|---|---|---|---|
| 4,741,736 A * | 5/1988 | Brown | A61M 5/142 604/131 |
| 5,100,380 A | 3/1992 | Epstein et al. | |
| 5,368,562 A * | 11/1994 | Blomquist | A61M 5/172 604/246 |
| 5,370,622 A * | 12/1994 | Livingston | A45C 11/22 224/247 |
| 5,573,506 A * | 11/1996 | Vasko | A61M 5/172 604/65 |
| 5,853,386 A * | 12/1998 | Davis | A61M 5/16854 604/65 |
| 6,305,908 B1 * | 10/2001 | Hermann | A61M 5/14244 417/234 |
| 7,734,323 B2 * | 6/2010 | Blomquist | A61M 5/14244 600/347 |
| 8,043,277 B2 | 10/2011 | Junker | |
| 8,888,738 B2 | 11/2014 | Gillespie, Jr. et al. | |
| 2006/0089619 A1 * | 4/2006 | Ginggen | A61M 5/14276 604/891.1 |
| 2011/0004188 A1 | 1/2011 | Shekalim | |
| 2011/0060284 A1 * | 3/2011 | Harr | A61M 5/14244 604/153 |
| 2013/0332874 A1 * | 12/2013 | Rosinko | G06F 3/0484 715/771 |

OTHER PUBLICATIONS

May 11, 2017 Written Opinion issued in International Application No. PCT/AU2017/050019.

Supplementary European Search Report re Application No. EP 17738037.5, dated Sep. 20, 2019.

* cited by examiner

INFUSION DEVICE

CROSS REFERENCE TO RELATED APPLICATIONS

This application is a continuation of PCT International Application No. PCT/AU2017/050019 filed on Jan. 12, 2017 which claims the benefit of priority from Australian Patent Application No. 2016900078 filed on Jan. 12, 2016, the contents of each of which are hereby incorporated in their entireties by reference.

BACKGROUND

Some embodiments relate to infusion devices and methods for their use and manufacture, in particular, portable devices and protective housings that reliably and include or consistently administer fluids and are configured to provide at least partial resistance to damage, shock, heat, tampering, user error and/or the ingress of water or particulate matter.

A wide variety of infusion pumps are now available to accommodate the growing number of medical indications requiring in-line fluid administration. Modern pharmaceutical treatments now indicate uses involving a wide range of compounds from very small molecules to very large compounds and biologics. A wider variety of dosage regimens are more frequently indicated, including very small to very large doses, very small to very large volumes, continuous doses over very short periods to much longer periods, or very specific regimens for administration of pharmaceutical combinations.

Many in-line pharmaceutical treatments are administered over extended periods requiring infusion via ambulatory infusion pumps rather than stationary infusion pumps, which are commonly used in hospital settings. In addition to the benefit of allowing patient mobility away from the bedside, ambulatory infusion pumps also provide the additional advantage of allowing patients to be treated in specialized clinics, in home or as hospital outpatients.

Ambulatory infusion pumps are generally smaller than stationary infusion pumps and are either mechanically driven pumps or battery fueled, electrically driven pumps. Most are simply portable units while very few, if any, are wearable devices able to unobtrusively integrate into the patient's usual lifestyle routines.

The most commonly used mechanical infusion pumps are elastomeric infusion pumps. These generally include a stretchable elastomeric reservoir that drives fluid under pressure through a flow restrictor, usually within the tubing of the patient's administration set, to regulate the rate of administration of the fluid to the patient.

SUMMARY

However, a number of environmental conditions may alter the flow rate administered via elastomeric pumps. Hypobaric conditions can decrease infusion rate (Mizuuchi, M and Namiki, A, 2003), variations in temperature, viscosity, duration of storage, back pressure, atmospheric pressure and partial filling can also effect flow rate (Skryabina, E A and Dunn, T S, 2006; Irish Medicines Board, 2008), overfilling or underfilling the infusion ball can vary infusion rate, bringing the flow restrictor in the patient's administration set into contact with cold, or the taping of the filter (Grissinger, M, 2013). Indeed, the partial filling of disposable pumps results in reported inaccuracies of up to 34% in delivery rate. (Skryabina, E A and Dunn, T S, 2006).

While theoretically not a gravity fed system, the flow rate administered via an elastomeric pump can vary if the reservoir is placed above or below the patient (termed the 'head height effect'). Patients using these devices also suffer from a pressure spike toward the end of the infusion resulting in a higher rate of administration to the patient.

It is therefore not surprising that a significant number of outpatients receiving treatment via elastomeric pumps rebound to hospital as a result of over or under dosage. While many device's product information reports a dosage accuracy range of +/−10%, in the clinical setting the actual variability in dosage rate to the patient may be up to +/−40% (Skryabina, E A and Dunn, T S, 2006; Irish Medicines Board, 2008). In addition, the infusion time may vary by 50% to 150% (Skryabina, E A and Dunn, T S, 2006).

Significant concerns exist in the safety of elastomeric pump use for infusing medications with narrow therapeutic windows such as nerve blocks (Ganapathy et. al., 2000), and cytotoxic drugs (Thornton, P, 2015; Institute for Safe Medication Practices Canada, 2015; Skryabina, E A and Dunn, T S, 2006).

Despite these difficulties, elastomeric infusion pumps are still widely used as they are simple to operate and therefore offer reliability of functioning over consistency of dosage; they are inexpensive, single use, disposable devices.

Many electric infusion pumps offer much greater accuracy than elastomeric infusion pumps. Many pumping mechanisms are suitable for use in these devices; of these, peristaltic mechanisms are possibly the most common.

Peristaltic pumping mechanisms may be linear or rotary and include a set of moving fingers, rollers or cams which section off a volume of fluid and propel it through the patient's administration set. The rate of delivery of fluid to the patient is controlled by the size of the fingers, rollers or cams, by restrictors or other flow rate adjustors added to the system, and the speed at which the fingers, rollers or cams move.

Syringe pumps offer a common alternative to peristaltic mechanisms and include a piston, cylinder and valve assembly. A motor drives the piston to dispense the fluid contained in the cylinder through the patient's administration set. The rate of delivery to the patient is controlled by the speed of the motor driving the piston. However, friction between the piston and the cylinder can cause a jerking effect known as 'stiction', whereby the infusing fluid is delivered in small boluses.

When used correctly, electrically driven infusion pumps offer much greater accuracy than elastomeric pumps. They are designed as reusable, programmable units, thus the electronic componentry involved increases the bulk of the unit and the cost of manufacture. Despite the operational accuracy of electrically driven infusion pumps, the complexity involved in programming units results in many instances of user programming error. Significant safety risks therefore arise from the use of these devices, particularly in ambulatory settings where medical professionals may not be immediately at hand.

In the United Kingdom, of the fifteen million infusions performed every year 700 unsafe incidents were reported with 19% attributed to user error (NPSA, 2004). In addition, about 60-65% of devices were identified as sitting idle most of the time (NPSA, 2004).

Additional safety concerns in the use of electronic devices have arisen from 'free flow' incidents whereby incorrectly fitted administration sets combined with rollers, fingers or cams inadvertently left in the open position have resulted in the gravity feeding of fluid to the patient at much greater administration rates than those prescribed. Mechanisms such as fork clamps and valves have been incorporated into administration sets to avoid these incidents, however these fixes fall well short of providing fail-safes.

Between 2005 and 2009, 87 infusion pump products were recalled in the United States alone (USFDA, 2010). Of these, 14 recalls were Class 1 recalls (which involve a reasonable probability that use of the recalled device will cause serious adverse health consequences or death) and 70 were Class 2 recalls (which may cause temporary or medically reversible adverse health consequences or involve the remote probability of serious adverse health consequences). In addition, 56,000 reports were made in the United States during this period of adverse events relating to the use of infusion pumps (USFDA, 2010). Further investigation by the United States Food and Drug Administration (USFDA) has identified the cause of many of the deficiencies leading to the recalls as resulting from the design and engineering of infusion pumps.

In Australia, a number of devices have also been recalled by the Therapeutic Goods Administration for safety concerns.

Safety still remains a major concern for infusion pumps. While accuracy remains a significant issue for elastomeric pumps, failure rates of electric pumps still remain high.

'Smart pumps' have emerged in an effort to improve the safety of electric infusion pumping devices. These include alarms to automatically trigger warning signals and/or safety protocols when incidents occur, such as the detection of air or an occlusion in the administration set, or when the fluid vessel is empty. However, immediate access to personnel of ordinary skill may be required to rectify the error and resume the correct administration protocol.

Improvements in pumping mechanisms, including the use of stepper motors, DC motors and motor-load sensors, and power supplies, including the use of switch-mode voltage regulators, low dropout linear regulators, which in turn improve performance and enable the use of sophisticated microprocessors, have been made to improve the safety of these devices.

However as the sophistication of electric infusion pumps grows, so too does the need for specialized personnel to maintain and operate the devices. Complex interfaces for programming administration regimens can confuse operators, particularly those involving unclear instructions, warnings messages or unexpected alarms. Sophisticated instrumentation involving complex processing also exposes these devices to potential software failure, which had been noted by the USFDA as the source of a cohort of infusion pump malfunctions (USFDA, 2010).

Commercially available instruments of this kind are inherently costly, unsuitable for self-administration or for use by operators not of ordinary skill, and are poorly adapted for the miniaturization desired to be unobtrusive to the patient. In addition, reusable, non-serializable instruments of this kind are unsuitable for use during surgeries and have therefore not displaced elastomeric infusion pumps as the pump of choice where the patient's risk of infection is high, such as during surgery.

It may therefore be beneficial to provide a cost-effective alternative to elastomeric infusion pumps and electronic infusion pumps that can to simply and reliably administer a include or consistent rate of fluid to a patient from an external vessel via an administration set, wherein the unit can be appropriately sanitized for its intended use.

In a first aspect, some embodiments relate to a portable device for transferring fluids from an external source and controllably infusing the fluids into a patient including;
an infusion line in for transporting fluid from the external source, an infusion line out for transporting fluid to the patient,
a protective housing containing therein
 at least one aperture for passing an infusion line in or an infusion line out therethrough,
 a pump unit for controllably drawing fluid through the infusion line in or controllably expelling fluid through the infusion line out,
 a computer in communication with the pump unit, a portable fuel source, and
 a computer programming interface, and
a seal for securing the contents of the protective housing therein.

In a second aspect, some embodiments relate to a portable device for transferring fluids from an external source and controllably infusing the fluids into a patient including;
an infusion pump housing for encasing an infusion pump mechanism therein, the infusion pump housing further including;
 a first protective housing piece including one or more apertures for receiving at least one length of infusion tubing therethrough, the first protective housing piece further defining a cavity and,
 an infusion pump mechanism at least partially located within the cavity, and
 a seal for securing the contents of the first protective housing piece therein,
wherein the seal is capable of forming a substantially water-resistant seal that allows the portable device to be sterilized when the seal is engaged.

In a preferred or advantageous form of the second aspect, portable devices of some embodiments advantageously or preferably include an infusion pump housing wherein the seal includes;
 a second protective housing piece,
 a sealing ridge substantially encircling the perimeter of the cavity, and
 a coupler for securing the second protective housing piece to the first protective housing piece wherein the sealing ridge is formed therebetween providing a substantially water-resistant seal between the second protective housing piece and the first protective housing piece when the coupler is engaged.

In a third aspect, some embodiments relate to a portable device for transferring fluids from an external source and controllably infusing the fluids into a patient including;
an infusion pump housing for encasing an infusion pump mechanism therein, the infusion pump housing further including;
 a first protective housing piece including one or more apertures for receiving at least one length of infusion tubing therethrough, the first protective housing piece further defining a first cavity,
 a first seal for securing the contents of the first protective housing piece therein,
 a second protective housing piece defining a second cavity,
 a second seal for securing the contents of the second protective housing piece therein,
an infusion pump mechanism at least partially located within the first cavity and at least partially located within the second cavity, and a coupler for coupling the first protective housing piece with the second protective housing piece, wherein each seal is capable of forming a substantially water-resistant seal that allows the portable device to be sterilized when each seal is engaged.

In a preferred or advantageous form of the second and third aspects, portable devices of some embodiments advantageously or preferably include an infusion pump mechanism further including;
   a pump unit,
   a computer in communication with the pump unit, and a portable fuel source.

In one form of some embodiments, the portable device and administration set include a single unit, advantageously or preferably a single use, disposable unit.

In preferred or advantageous forms of the second and third aspects, the first protective housing piece of the portable device includes an infusion pump cassette.

In preferred or advantageous forms of the second and third aspects, the pump unit and the computer in communication with the pump unit are substantially located within the second cavity of the second protective housing.

The protective housing preferably or advantageously protects the contents located therein and provides at least partial resistance to damage, shock, heat, tampering, user error and/or the ingress of water or particulate matter.

When the coupler is engaged, the portable device cannot be easily opened. Thus, in an advantageous or preferred form, the protective housing includes an opening groove for prising the second housing piece and protective housing apart.

In a preferred or advantageous form, an opening tool may be required to prise the second housing piece and the protective housing apart, so as to render the operation of the portable device substantially protected from tampering and/or user error.

A seal in accordance with aspects of some embodiments may include any methods capable of sealing a housing from the external environment so as to contain the contents therein separately from the external environment. It may include, for instance, a rubber or silicon seal, an o-ring, a rubber or silicon ridge or the like. A seal may be capable of securing the contents of the protective housing therein or may be capable of forming a substantially water-resistant seal that allows the portable device to be sterilized when the seal is engaged.

In a preferred or advantageous form of a portable device according to the second or third aspects, the seal advantageously or preferably includes an annular o-ring substantially encircling the perimeter of the cavity of a housing piece. However, in an alternative preferred or advantageous form of a portable device, the seal may include a sealing ridge substantially encircling the perimeter of the cavity. Advantageous or preferably, the seal includes a silicon seal.

Advantageously or preferably, the seal further includes an annular channel substantially encircling the perimeter of the cavity, which corresponds with the placement of the annual o-ring or sealing ridge for sealing the device. For certain embodiments this annular channel enables a housing to be sealed to render the portable device water resistance and, optionally, stabilizable.

In certain embodiments, an annular channel substantially encircling the perimeter of the cavity is provided on a first protective housing piece and a second protective housing piece. Both channels may further correspond with the placement of an annular o-ring for sealing the device.

An alternative protective housing according to some embodiments advantageously or preferably includes a sealing ridge substantially encircling the pump unit, computer, portable fuel source and computer programming interface. When the coupler is engaged, the sealing ridge advantageously or preferably forms a seal between the second housing piece and the protective housing. Advantageously or preferably, the seal substantially prevents the ingress of water or particulate matter within the protective housing.

Advantageously or preferably, the sealing ridge is attached to or formed integrally with the protective housing.

In alternative forms of some embodiments, the seal may include a potting material. Advantageously or preferably, the potting material is a silicon based potting material.

Suitable potting materials according to some embodiments may include thermo-setting plastics or silicone rubber gels, for example polyurethane potting, silicone potting, epoxy resin potting, adhesive potting compounds or combinations thereof. Silicones or epoxy resins are advantageous or preferred for protecting against the loosening of wires or from impact. Advantageous or preferred potting materials include materials less susceptible to shrinking upon cooling. This ensures that the potting material creates a substantially water-resistant barrier, prevents the ingress of moisture within the portable device and/or enables the portable device to be sterilized according to methods accepted by medical practice.

The protective housing may be formed from a substantially impervious material. It is advantageously or preferably formed from a firm or rigid material which may additionally provide some cushioning or shock absorption. The material may be chemically inert, biologically inert, of medical grade, and/or suitable for standard medical waste disposal.

Advantageously or preferably, the material is adapted to withstand temperatures in the range of 10° C. to 40° C., atmospheric relative humidity in the range of 10% to 90% humidity non-condensing and/or an atmospheric pressure in the range of 695 to 1000 hPa.

Advantageously or preferably, the material must or should be able to withstand chemical attack by chlorinated or ethanol-based products and/or other chemicals commonly found in medical or domestic cleaning agents.

Advantageously or preferably, the protective housing is formed from silicon.

The protective housing may be wearable, thus it's shape may be configured to be small and discreet when attached to the patient's body, held in hand or carried in the patient's pocket. The protective housing is advantageously or preferably a flattened shape. The portable housing is non-implantable.

In a preferred or advantageous form, the protective housing is generally palm sized. Advantageous or preferably, the protective housing is less than approximately 15 cm in length, 10 cm in width and 3 cm in height. Most advantageously or preferably, the protective housing is approximately 6.4 cm in length, 4.8 cm in width and 1.7 cm in height.

Advantageously or preferably, the device weighs less than about 100 g and more advantageously or preferably less than about 61 g (including the device and the infusion line(s)).

In a preferred or advantageous form, the protective housing may be opaque but provides sufficient transparency to allow light to pass therethrough.

Advantageous or preferably, the portable device includes an internal chassis wherein the internal chassis is located within the protective housing. In alternative forms of some embodiments, a cavity of a first protective housing piece and/or a second protective housing piece may include an internal chassis. In a preferred or advantageous form, the infusion pump mechanism is at least partially located within the internal chassis. In certain preferred or advantageous forms, the internal chassis substantially maintains the pump unit, the computer, the portable fuel source and the computer programming interface in place.

In one form, the internal chassis may be formed from potting material. The internal chassis may be formed by pouring liquefied potting material into the cavity defined by the protective housing, which is then allowed to harden.

Alternatively, the internal chassis may define cavities or openings therein. The cavities or openings may be shaped to receive the pump unit, computer, and computer programming interface, thus the internal chassis advantageously or preferably substantially contains the pump unit, computer and computer programming interface.

The internal chassis may guide the placement of the of the pump unit, computer and computer programming interface within the portable device and any physical connections formed between them. The internal chassis may, further, be configured to substantially maintain the pump unit, computer and computer programming interface and any physical connections formed between them in a desired position. The internal chassis may also be configured to maintain a battery and/or microSD card and any physical connections formed between them, and other components, in a desired position. In doing so, the internal chassis may provide the internal components of the portable device with greater protection from damage sustained as a result of motion or shock.

The internal chassis may further include one or more apertures formed therethrough for passing a length of infusion tubing through the apertures. In this configuration, a length of infusion tubing may pass through the internal chassis to engage with the pump unit.

In a preferred or advantageous form, the internal chassis may be formed from a material that provides some cushioning or shock absorbance. Suitable materials may include antistatic and non-combustible foams, rubbers, silicons and/or other composite materials.

Advantageous or preferred internal chasses may maintain a pump mechanism therein. Pump mechanisms according to some embodiments may include the combined components of a functional pump; for instance, a pump unit, an actuator, a computer, a fuel source, etc.

In one form of some embodiments, the pump unit includes an actuator and a pump. The pump may include any one of a number of micro pumps that are known in the art and would be understood by persons of ordinary skill in the art to be suitable for use in a pump unit according to some embodiments. Advantageous or preferred pumps include diaphragm pumps (e.g. microdiaphragm pumps), peristaltic pumps (which are well known in the art), or syringe pumps (also known as syringe drivers). Suitable actuators to couple with the pump of choice will be known to persons of ordinary skill in the art. Indeed, many commercially available pumps are purchased with a well-matched actuator.

Advantageous or preferred pumps may be selected depending on their suitability for meeting the requirements of the administration regimen. For instance, a syringe pump may be advantageous or preferred for the administration of small specific doses of a medicament. However, a peristaltic pump may be advantageous or preferred for the administration of a larger volume over a prolonged period of time.

Advantageously or preferably, portable devices according to some embodiments include a sensor. Optionally, the pump unit may include a sensor. Suitable sensors will include those known to persons of ordinary skill in the art to be suitable for the sensing of flow rates and pressure changes.

Sensors may therefore be utilized to trigger malfunction alarms or to modulate the action of the actuator under the control of the computer. Thus, the sensor may communicate with the computer (e.g. to provide feedback on the operation of the pump).

Alternatively, a pressure sensor may be used, for instance, as an occlusion sensor.

A preferred or advantageous pump includes a piezoelectric pump, optionally including a piezoelectric actuator and piezoelectric sensor.

In one form of some embodiments, the infusion line in and the infusion line out may include a single line. This form may be advantageous or preferred for some embodiments, for example, those including a peristaltic pump.

For embodiments utilizing other pumps, for example those utilising diaphragm or syringe driver pumps, the infusion line in may include a first line engaging with the external source of fluid at one end and the pump unit at the other end, and/or the infusion line out may include a second line engaging with the pump unit at one end and the patient's vascular access device at the other end.

The infusion line in and the infusion line out may terminate in a coupling or closure fitting. Advantageous or preferable couplings include those that correspond with fittings found on suitable infusion vessels (e.g. infusion bags), vascular access devices (e.g., midline, central, intrathecal etc.) and/or other in line devices such as intravenous filters or valves (e.g. inline check valves). Advantageously or preferably, the infusion line in and infusion line out terminate in a leur lock coupling.

Advantageous or preferred infusion lines in and infusion lines out are formed from materials known to persons of ordinary skill in the art to be suitable for carrying medicinal fluids. Advantageously or preferably, such vessels are formed from chemically and biologically inert materials, high drug stability materials, medical grade materials and/or must or should be suitable for standard medical waste disposal practices.

High drug stability materials known to be suitable for forming infusion lines may include polyvinylchloride, polyolefin, ethylene-vinyl acetate and polypropylene based materials.

The pump unit advantageously or preferably controls the rate of flow of fluid through the infusion line in and/or infusion line out via the computer. The computer advantageously or preferably includes a memory unit, a processor and/or a power supply. Suitable computers for use as on-board portable device computers will be known to persons of ordinary skill in the art based on the selection of pump unit components and sensors.

Advantageously or preferably, the infusion pump mechanism of a portable device according to some embodiments includes a computer programming interface. In advantageous or preferred forms of the third aspect, the computer programming interface is substantially located within the second cavity. Advantageous or preferred computer programming interfaces include internal computer programming interface.

Internal programming interfaces include interfaces that do not enable the programming of the infusion regimen from the exterior surface of the infusion device housing. In particular, they do not include buttons or switches to enter infusion regimen values.

Advantageously or preferably, the computer programming interface includes an interface at which the computer receives a user's instruction on how to set and/or to modulate the activity of pump unit, or more specifically, the actuator (e.g. by programming a fixed flow rate or regimen of flow rates or rules for the modulation of flow rates in certain circumstance). The computer programming interface may be adapted for exclusive programming by a manufacturer, a clinician and/or technician.

Advantageously or preferably, the internal computer programming interface of the portable device includes a non-tamperable computer programming interface. In particular, non-tamperable computer programming interfaces include interfaces that will not permit an infusion program to be altered or amended once the infusion program has commenced.

The internal computer programming interface may also include a non-editable computer programming interface. In particular, non-editable computer programming interfaces include interfaces that will not permit an infusion program to be altered or amended once the program has been entered.

A preferred or advantageous non-tamperable or non-editable computer programming interface may permit the selection of pre-set series of infusion programs. A preferred or advantageous internal computer programming interface may include a memory device reader.

In one form, the computer and computer programming interface may be formed integrally.

Alternatively, the computer and computer programming interface may be separate components connected electronically or digitally. For example, where the computer programming interface is a memory device reader, the reader may include a separate component in electronic or digital communication with the computer.

Advantageous or preferred memory device readers include those capable of reading a removable memory device. Particularly advantageous or preferred memory devices readers include microSD readers.

A removable memory device may be used to pre-program a fluid administration regimen or to program additional rules to improve the safety of a fluid administration regimen.

Alternatively, the computer and computer programming interface may be formed integrally wherein the fluid administration regimen is programmed remotely from the portable device and is transmitted to the computer programming interface via a digital signal. Advantageously or preferably, the fluid administration regimen is programmed at a remote user interface. The signal may be transmitted wirelessly via various devices including Bluetooth, telecommunications or satellite signals, infrared signals, RFID signals or body area networks. Advantageous or preferably, the remote user interface is located on a computer or mobile device and is advantageously or preferably transmitted via secure and/or encrypted telecommunications networks.

In an alternative form, the computer in communication with the pump unit may be pre-programmed. In this alternative form, the computer programming interface may be optional. The computer may be pre-programmed so as to render the pump non-tamperable and/or non-editable.

As the computer programming interface is located within the protective housing, the pump unit may be substantially protected from tampering and/or user error once in operation.

Thus, the protective housing may not require, and in a preferred or advantageous form, may not include a digital user interface. Alternatively, the protective housing may include a remote digital user interface.

The portable device may further include a switch or button underlying the protective housing. The switch or button may be engaged by a user through the housing to start or stop the device, to initiate priming of the infusion regimen, or initiate a safety sequence in the event of malfunction.

However, a switch or button may not be necessary. For instance, in forms of some embodiments according to the second or third aspects, engagement of the first protective housing piece with the second protective housing piece may initiate the infusion regimen. This may be advantageous or preferred in embodiments wherein the first protective housing piece of the portable device includes an infusion pump cassette. In particular, a first protective housing piece including a portable fuel source may be engaged with a second protective housing piece including a computer and, optionally a pump unit, to fuel the computer and/or pump and thereby initiate its operation.

The portable device may further include an indication light underlying the protective housing, to indicate operation of the pump unit. Advantageously or preferably, the indication light is a static LED light and optionally changes color or intensity depending on the status of the pump (e.g., pause=red; on=green or on=static light; pause=flashing light).

For instance, a removable memory device may be pre-programmed via an external computer by a manufacturer, clinician and/or technician according to a desired administration regimen.

The memory device may be engaged with the memory device reader and the administration lines fitted in the pump mechanism. The portable device componentry may be placed within the protective housing and the protective housing filled with liquefied potting material which, upon hardening, creates a water resistance seal suitable for sterilization.

Alternatively, the memory device may be placed in a corresponding inner chassis cavity to engage with the memory device reader. The second housing piece and protective housing may be engaged to form a seal around the sealing ridge, which is held in place by engaging the coupler to secure the protective housing.

Infusion may be commenced via the activation switch or button which initiates the computer to process the administration regimen (stored in the memory device or computer) and engage the actuator to apply pumping pressure to commence infusion according to the administration regimen.

In advantageous or preferred portable devices of the second and third aspects the portable fuel source is substantially located within the first cavity of the first housing piece.

The portable fuel source may include any number of miniature portable fuel sources known to persons of ordinary skill in the art, such as kinetic energy generators or solar energy generators. Advantageously or preferably these are coupled with fuel cells to store energy generated during use.

In a preferred or advantageous form, the portable fuel source includes a battery. Advantageous or preferred batteries must or should be capable of maintaining charge for at least 24 hours at a flow rate of 10 ml/hour, advantageously or preferably at least 48 hours at a flow rate of 10 ml/hour.

In a preferred or advantageous form, the battery is connected to the computer and the pump unit to fuel operation of these components.

In a fourth aspect, some embodiments relate to a method for controllably infusing a prepared solution into a patient including;

obtaining a vessel containing the prepared solution, obtaining an external memory device, programming the external memory device with a desired administration regimen for controllably infusing the prepared solution, engaging the external memory device with a memory device reader according to some embodiments, obtaining a portable device according to some embodiments further including the external memory device, connecting the infusion line in to the vessel, connecting the infusion line out to the patient, and activating the portable device, wherein the pump unit controllably draws the prepared solution through the infusion line in and/or controllably expels the prepared solution through the infusion line out at a rate set by the administration regimen and stored on the external memory device.

The external source of fluid according to some embodiments may include any one of a number of vessels know to persons of ordinary skill in the art to be suitable for carrying medicinal fluids. Advantageously or preferably, such vessels are formed from chemically and biologically inert materials, medical grade materials and/or must or should be suitable for standard medical waste disposal practices. Advantageously or preferably, the vessel includes an infusion bag.

Once the sealed vessel (e.g. an infusion bag) containing the prepared solution has been obtained, a portable device according to some embodiments and an external memory device (e.g. microSD card) have been obtained, the infusion line in may be connected with the sealed vessel via a suitable coupling (e.g. a leur lock coupling). The infusion line in may include an external clamp to prevent the passage of the prepared solution to the portable device.

The external memory device may be prepared for use with the portable device by recording a desired administration regimen to the device in the desired format. This may be performed by the manufacturer, the clinician, a technician and/or by the user. Alternatively, a first programmer (e.g., the manufacturer) may pre-program a set of commonly used administration regimen for frequently administered medications whereby a second programmer (e.g., a clinician) may simply select the desired pre-prepared administration regimen which is recorded in the desired format. In a further alternative form, the second programmer (e.g., a clinician or patient) may select from the commonly used administration regimes via the switch or button underlying the protective housing.

Advantageously or preferably, a single administration regimen is programmed to a single external memory device. For example, an administration regimen may include the administration of fluid at a rate of about 10 ml/hour, about 5 ml/hour, or a set variable rate.

The external memory device may also be prepared by recording one or more safety rules, updates or improvements that may be executed in the event of malfunction.

Advantageously or preferably, methods of the fourth aspect may include the step of executing one or more safety rules. Safety rules may include rules that are undertaken in the event of device malfunction. Advantageously or preferred rules include a rule whereby a maximum flow rate is limited by a redundant action, for example the cessation of the pump or actuator or disengagement of the fuel source. For instance, a rule preventing the pumping of fluid beyond a maximum pressure of, for example 1200 mmHg, may be included in the safety rules. In addition, a rule preventing backflow may also be included in the safety rules. Optionally, an alarm may signal when a malfunction event occurs.

Further safety rules advantageously or preferably include those occurring in the event of a downstream occlusion or an upstream occlusion. A preferred or advantageous rule includes a rule whereby the pump unit pauses and stops pumping when the line pressure is 825 mmHg (160 kPa)+/− 375 mmHg16 (50 kPa). Optionally, an alarm may signal when such an event occurs. The safety rule may also include a rule whereby the pump unit may resume once the occlusion is removed.

Advantageous or preferred safety rules may include rules whereby the pump unit pauses and stops pumping when air in line is sensed. Optionally, an alarm may signal when such an event occurs. The safety rule may also include a rule whereby the pump unit may resume once the air is removed, e.g., by an in-line filter.

The configuration and use of the external memory device may be readily adapted to meet the requirements of the manufacturer, clinician or patient. For instance, the preparation of the external memory device may be adapted to the use of the portable device as a single use device.

Furthermore, the content recorded to the external memory device may not only include the flow rate to be administered, the duration of infusion and total volume of infusion, it may also record other variables specific to the patient's therapy, such as the indication of use, the identity of the medicinal compound and solvent, the viscosity of the solution, details of combined therapies and the like.

Advantageous or preferred flow rates include those substantially ranging between about 1.5 ml/hour and 10 ml/hour. Advantageously or preferably, the flow rates achieved will be at least about +/−6% of the desired flow rate and may be at least about +/−2% of the set flow rate.

Advantageously or preferably, flow rates may be continuous wherein the average flow rate over a five minute period falls within the set range or on the set flow rate within an allowable tolerance.

Advantageously or preferably, the portable device may adjust to the administration of fluids within a wide range of viscosities. The flow rate may be self-adjusting for the administration of fluids with viscosities within the range of about 0.7 $mm^2/s$ to 1.7 $mm^2/s$.

Advantageously or preferably, the portable device includes a "keep line open" function, such that when the administration regimen is complete, the pump unit infuses fluid at a flow rate of either the lowest programmed flow rate or 0.5 ml/hour for about four hours.

Advantageously or preferably, the pump unit will continue to infuse until the fluid is consumed. Thus, the pump unit will advantageously or preferably detect when no fluid is available to infuse. Further, the pump unit will advantageously or preferably distinguish between air in the line and an empty fluid source.

Methods according to some embodiments may also include a line priming step. Advantageously or preferably, the line priming procedure is executed automatically according to a programmed routine.

Prior to engaging the coupler, the sealing ridge may be carefully positioned between the second housing piece and the protective housing to form a barrier surrounding the pump unit, computer, portable fuel source and computer programming interface and any other electronic components located therein. By engaging the coupler, which may include any number of suitable clips or closures, the barrier creates a seal to substantially prevent the ingress of water or particulate matter into the protective housing.

To form an effective seal; glue, adhesive, grease or lubricant may be applied to the sealing ridge.

In a preferred or advantageous form, a sealing ridge is attached to or formed integrally with the protective housing, and the coupler includes a cavity corresponding to the shape of the sealing ridge, formed in the second housing piece. Thus, when the second housing piece and the protective housing are brought together, the fit of the sealing ridge within the coupler maintains a firm closure of the protective housing.

Once the external memory device has been engaged with the memory device reader and the protective housing has been securely closed, the infusion line out may be connected to a patient's vascular access device via a suitable coupling (e.g., a leur lock coupling).

To activate the portable device, the switch or button underlying the protective housing may be engaged to start the device, and the external clamp on the infusion line in may be released allowing free flow to the pump.

In a fifth aspect, some embodiments relate to an infusion pump housing for encasing an infusion pump mechanism therein including;
a protective housing piece defining a cavity for maintaining the infusion pump mechanism at least partially therein further including;
one or more apertures formed through the protective housing piece for receiving at least one length of infusion tubing therethrough, and
a seal for securing the contents of the protective housing piece therein,
wherein the seal is capable of forming a substantially water-resistant seal that allows the infusion pump housing to be sterilized when the seal is engaged.

In a preferred or advantageous form of the fifth aspect, some embodiments relate to an infusion pump housing wherein the seal includes a potting material.

In advantageous or preferred embodiments of the fifth aspect, some embodiments relate to an infusion pump housing wherein the seal includes; a second housing piece, a sealing ridge substantially encircling the perimeter of the cavity, and a coupler for securing the second housing piece to the protective housing piece wherein the sealing ridge is formed therebetween providing a substantially water resistant seal between the second housing piece and the protective housing piece when the coupler is engaged.

In one form, the infusion pump housing may be formed from a substantially impervious material. Advantageously or preferably, the infusion pump housing is formed from a material that is firm or rigid and may optionally provide some cushioning or shock absorption. Advantageously or preferably, the material is chemically inert, biologically inert, of medical grade, and/or is suitable for standard medical waste disposal.

Advantageously or preferably, the material is able to withstand temperatures in the range of 10° C. to 40° C., atmospheric relative humidity in the range of 10% to 90% humidity non-condensing and/or an atmospheric pressure in the range of 695 to 1000 hPa.

Advantageously or preferably, the material is able to withstand chemical attack by chlorinated or ethanol-based products and/or other chemicals commonly found in medical or domestic cleaning agents.

Advantageously or preferably, the infusion pump housing is formed from silicon.

The infusion pump housing may not require a digital user interface. In a preferred or advantageous form, the infusion pump housing may be opaque but provides sufficient transparency to allow light to pass therethrough.

As the infusion pump housing may be wearable, it's shape may be configured to be small and discreet when attached to the patient's body, held in hand or carried in the patient's pocket. The infusion pump housing is advantageously or preferably a flattened shape. The infusion pump housing is non-implantable.

In a preferred or advantageous form, the infusion pump housing is generally palm sized. Advantageously or preferably, the infusion pump housing is less than approximately 15 cm in length, 10 cm in width and 3 cm in height. Most advantageously or preferably, the infusion pump housing is approximately 6.4 cm in length, 4.8 cm in width and 1.7 cm in height.

In one form, the seal is attached to or formed integrally with the protective housing. In an alternative form, the seal is formed by placing an o-ring within a cavity formed in the protective housing. In a further alternative form, the seal is formed from hardened potting material, whereby the seal may be formed by pouring liquefied potting material into the protective housing cavity once the electronic componentry and line assembly have been placed within the protective housing.

Advantageously or preferably, the seal is formed from silicon or silicon rubber.

In a preferred or advantageous form of the infusion pump housing, the coupler may include any number of suitable clips or closures. Advantageously or preferably, the coupler includes a cavity corresponding to the shape of a sealing ridge, formed in the protective housing.

In one form, the second housing piece and protective housing both include a second shallower cavity substantially encircling the perimeter of the cavity wherein an o-ring may be placed therebetween.

In a preferred or advantageous form, the protective housing includes an opening groove for prising the second housing piece and protective housing apart. Optionally, an opening tool may be required to prise the second housing piece and the protective housing apart.

Advantageously or preferably, the infusion pump housing includes an internal chassis. The internal chassis is advantageously or preferably of a size and/or configuration to be contained within the protective housing.

The internal chassis is advantageously or preferably formed from potting material.

An alternative internal chassis advantageous or preferably defines cavities or openings therein. The cavities or openings may be shaped to receive the infusion pump mechanism. The cavities or openings may, further, be shaped to substantially maintain one or more components of the infusion pump mechanism and any physical connections formed between them. A cavity or opening may be shaped to receive a pump, a battery, a computer and a removable memory device.

In a preferred or advantageous form, the internal chassis is formed from a firm or rigid material that may also provide some cushioning or shock absorption.

In a preferred or advantageous form, the internal chassis is less than approximately 12 cm in length, 8 cm in width and 3 cm in height. Most advantageous or preferably, the infusion pump housing is approximately 5 cm in length, 3.5 cm in width and 1.5 cm in height.

In a sixth aspect, some embodiments relate to a method for manufacturing a portable device according to aspects of some embodiments including;

obtaining the protective housing, the infusion line in, the infusion line out, the pump unit, the computer, the portable fuel source, and the memory device reader of some embodiments, assembling the external memory device, the pump unit, the computer and the memory device reader of some embodiments, obtaining an external memory device, programming the external memory device with a desired administration regimen for infusing the fluids into a patient, engaging the external memory device with the memory device reader, placing the assembled external memory device, pump unit, computer, memory device reader, and external memory device substantially within the protective housing of the portable device, placing the infusion line in and the infusion line out through the protective housing, and engaging the seal of some embodiments to secure the contents of the protective housing therein.

In a seventh aspect, some embodiments relate to a method according to the sixth aspect wherein the step of engaging the seal of some embodiments to secure the contents of the protective housing therein includes;

pouring a potting material within the protective housing of the portable device, and allowing the potting material to harden therein.

In an eighth aspect, some embodiments relate to a method of assembling a portable infusion device including the steps of;

obtaining an infusion pump housing according to some embodiments, obtaining an infusion pump mechanism, placing the infusion pump mechanism at least partially within the cavity of the protective housing piece, obtaining at least one infusion line, connecting the infusion line to the infusion pump mechanism, placing the infusion line through the one or more apertures formed through the protective housing piece, and engaging the seal according to some embodiments wherein the seal forms a substantially water resistant seal that allows the assembled infusion device to be sterilized.

Advantageous or preferred methods according to some embodiments may include the step of sterilizing the portable device once the seal is engaged. In a preferred or advantageous form, the sterilization of the portable device includes the sterilization of the device with the patient's administration set assembled. Methods for sterilization include those well known in the art as being suitable for medical applications, particularly those well known for the sterilisation of administration sets.

To form an effective seal, glue, adhesive, grease or lubricant may optionally be applied to the seal.

Some embodiments now will be described with reference to the accompanying drawings together with the Examples and the advantageous or preferred embodiments disclosed in the Detailed Description. Some embodiments may take many different forms and should not be construed as limited to the embodiments described herein. These embodiments are provided by way of illustration only such that this disclosure will be thorough, complete and will convey the full scope and breadth of some embodiments.

DETAILED DESCRIPTION OF EXEMPLARY EMBODIMENTS

Examples

Several embodiments are described in the following examples.

Example 1—Infusion Pump Design

Figure 1A:
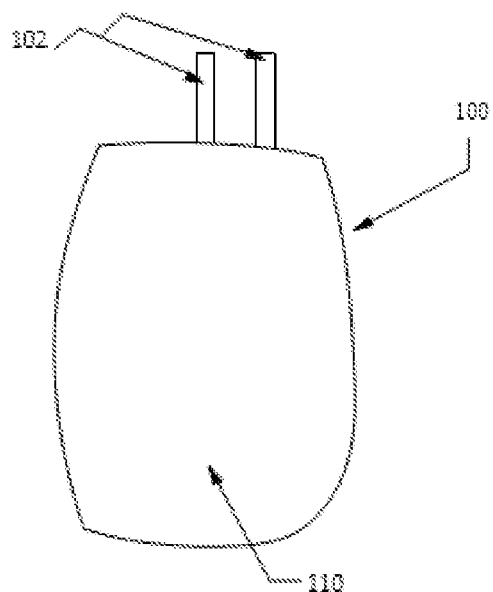
FIGS. 1a and 1b show a top plan view of an infusion pump of some embodiments with FIG. 1a showing a top plan view of the exterior housing of the pump and FIG. 1b showing a top plan view of the interior of the pump with the exterior housing removed.
Figure 1B:
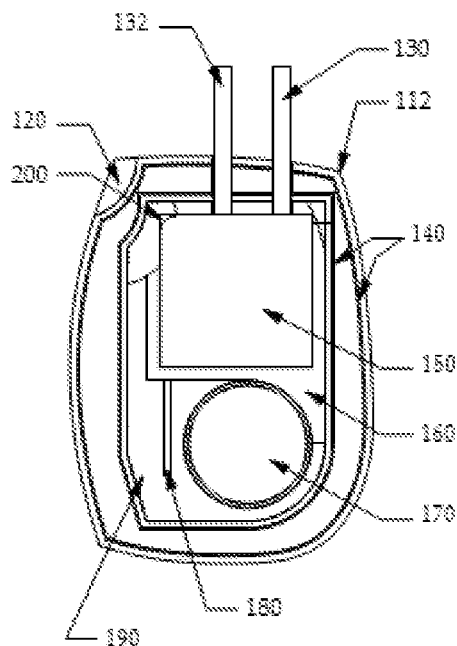

FIGS. 1a and 1b illustrate the infusion pump of some embodiments (100) showing the infusion lines (102) in connection with the pump. FIG. 1a shows the upper exterior housing of the pump (110) formed from silicon to provide a medically inert protective casing.

FIG. 1b shows the interior layout of the pump with the upper exterior housing (110) removed. The placement of the internal pump componentry is illustrated in FIG. 1b. The location of the outer case opening point is shown at 120, located in lower exterior housing (112). An infusion line in (130) is shown passing through the pump shown at 150 and an infusion line out (132) is shown exiting the pump at 150. Dual silicon seals spanning the perimeter of the pump exterior housing are shown at 140, a peristaltic pump is shown at 150, an inner chassis is shown at 160, a battery is shown at 170, a microSD card is shown at 180, and an on-board computer is shown at 190 including a circuit board, microprocessor and power supply (not shown). The location of the pump removal point, defined by a groove in the outer housing, is shown at 200.

The infusion lines in and out (130 and 132) terminate in a leur lock coupling. The infusion line in (130) is coupled with a patient's administration set including an in-line occlusion filter and a peripherally inserted central catheter line (PICC line) for vascular access.

Figure 2A:
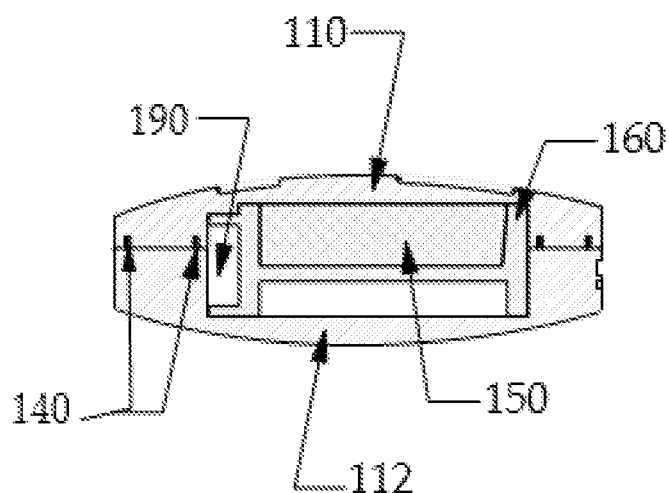
FIGS. 2a and 2b show a sectional view of an infusion pump of some embodiments with FIG. 2a showing a proximal section across the interior of the pump and FIG. 2b showing a distal section across the interior of the pump.
Figure 2B:
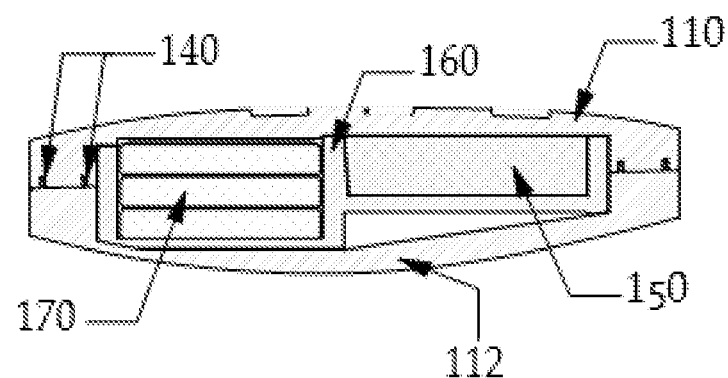

FIGS. 2a and 2b provide a sectional view of the infusion pump showing the placement of pump componentry across the proximal (FIG. 2a) and distal (FIG. 2b) ends of the pump. FIG. 2a provides a proximal view showing the location of the inner chassis (160) housing the pump componentry including the peristaltic pump (150) and the on-board computer (190). The location of the dual silicon seals are shown at 140 within the upper and lower exterior housing (110 and 112). FIG. 2b provides a distal view again showing a cross section of the inner chassis (160) revealing the distal conformation of the inner chassis. The inner chassis houses the peristaltic pump (150) along the entire length of the pump, as shown in the distal view, and is located adjacent to the battery (170) at the distal end of the infusion pump. The dual silicon seals (140), located within upper and lower exterior housing (110 and 112) encircle the inner chassis (160).

Figure 3A:
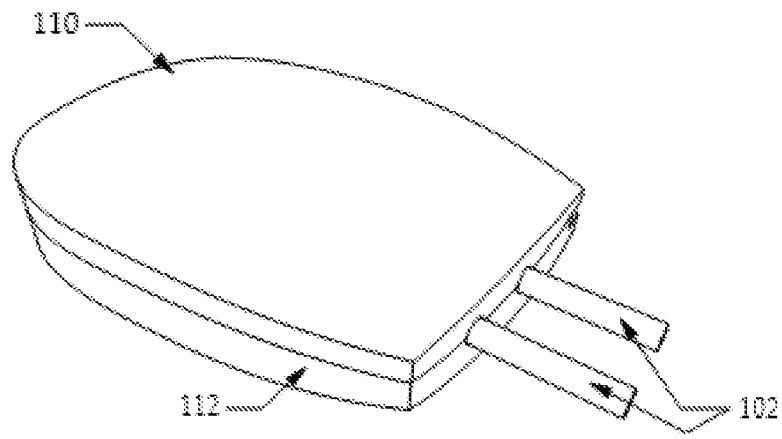
FIGS. 3a and 3b show a top perspective view of an infusion pump of some embodiments with FIG. 3a showing a left perspective view and FIG. 3b showing a right perspective view.
Figure 3B:
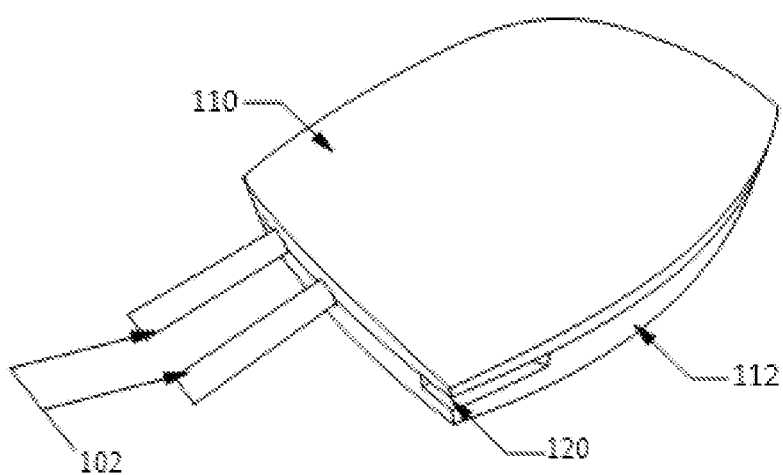

FIG. 3a provides a left perspective view of the pump showing the upper and lower exterior housing (110 and 112) sealed and enclosing the patient's infusion lines (102). The seal created by the silicon seals, and the upper and lower housing around the infusion lines (102) prevent the ingress of water and small particulate materials into the interior of the infusion pump. Grooves are formed within the silicone upper and lower exterior housing (110 and 112) during manufacture, such that the grooves will neatly and securely encircle standard diameter infusion tubing. FIG. 3b provides a right perspective view showing the outer case opening point (120) formed by an additional groove in the lower exterior housing (112). The outer case opening point (120) allows the sealed outer housing to be prised open for the secure placement of the patient's infusion line into the infusion pump.

Figure 4A:
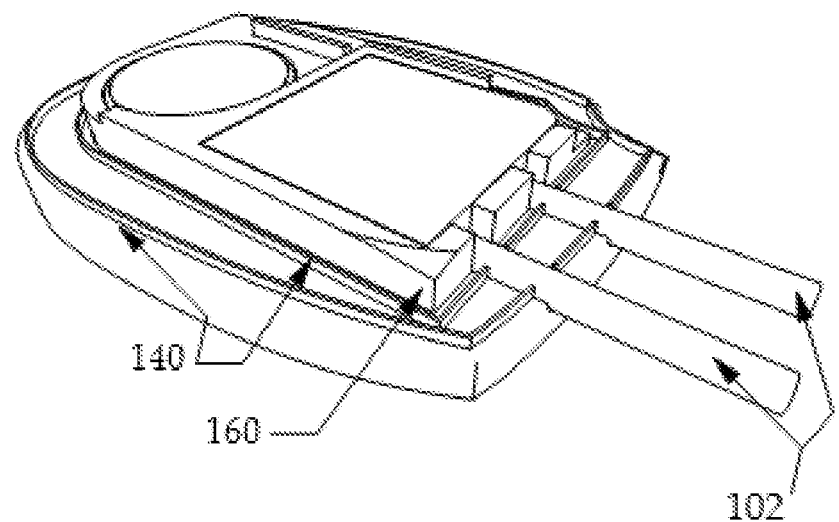
FIGS. 4a and 4b show a top perspective view of the interior of an infusion pump of some embodiments with FIG. 4a showing a left perspective view of the interior of the infusion pump and FIG. 4b showing a right perspective view of the interior of the infusion pump.

FIG. 4a shows a left perspective view of the interior of the pump with the upper exterior housing removed. The conformation of the inner chassis (160) is illustrated in detail which shows channels and cavities provided in the inner chassis for the secure placement of the infusion lines and pump componentry therein. As illustrated, the inner chassis provides for appropriate placement and additional protection and cushioning of the internal componentry of the pump to protect components, and connections between components, from impact damage. Dual silicon seals (140) encircle the inner chassis (160) to seal the chassis and componentry housed therein from moisture and small particulate material such as sand and dust. This provides additional protection to the internal componentry from damage caused by moisture or abrasion.

Figure 4B:
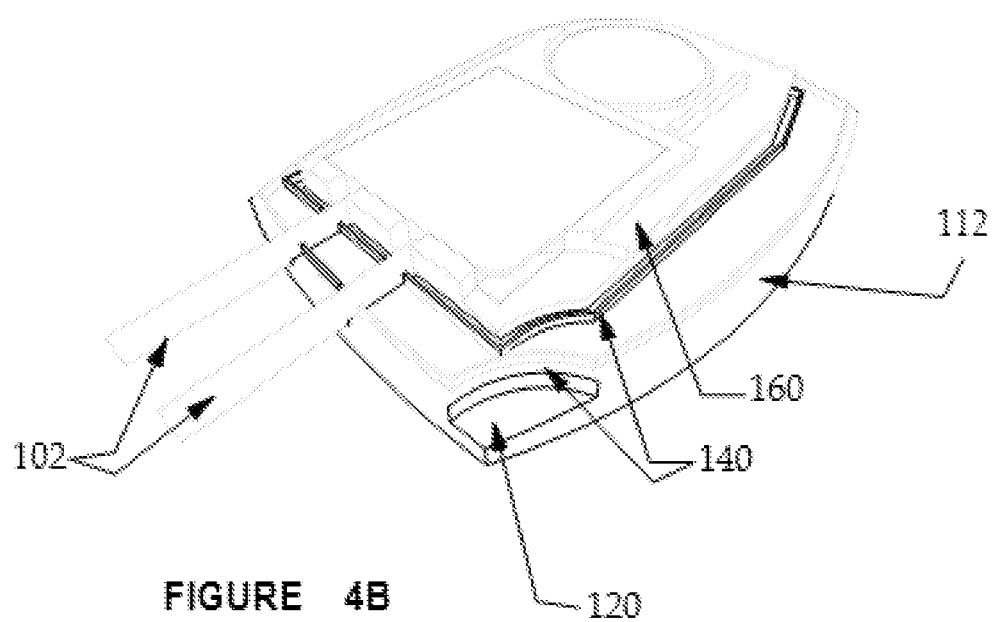

FIG. 4b shows a right-side perspective view of the interior of the pump depicting greater detail in the configuration and shape of the inner chassis (160) and dual silicon seals (140). At the right side, the inner chassis (160) provides an additional cut out for the secure placement of further componentry. Both the dual silicon seals (140) and the inner chassis (160) are shaped to accommodate the groove cut-away in the lower exterior housing (112) to provide the outer case opening point (120) while maintaining the structural integrity of the pump.

An alternative inner chassis may be formed from silicon potting compound (not shown). A potted chassis is formed following placement of the assembled mechanical and electrical componentry within the lower exterior housing. The silicon potting compound is formed and prepared for use according to the manufacturer's instructions and poured within the lower exterior housing to fill the lower exterior housing. The compound is then allowed to cure under conditions recommended by the manufacturer. The upper and lower exterior housing are then assembled in the usual manner described herein.

In this alternative form, the hardened potting compound performs in a similar manner to the fabricated chassis including cut away portions; fixing the placement of the mechanical and electrical componentry within the outer housing and providing cushioning and shock resistance to the infusion pump.

In a further alternative form, a silicon potting material may be used in place of the dual silicon seals and the inner chassis to prevent the ingress of moisture and small particulate material such as sand and dust, which may damage the pump componentry. The lower exterior housing may be formed to completely contain the pump componentry and the infusion lines passing through the housing therein. Once the mechanical and electrical componentry of the pump has been placed and assembled within the lower exterior housing, the infusion line is then placed within the pump. The lower exterior housing is filled with silicon potting compound until all of the components of the pump, and the infusion lines, are submerged in the silicon potting material. The potting material is again allowed to cure, at which time the upper exterior housing may be secured to the lower exterior housing by any one of many methods well known to persons of ordinary skill in the art (for example by using an appropriate silicon bonding agent). The upper exterior housing is effectively cosmetic, as the potting material forms an effective seal preventing the ingress of moisture or particulates to the pump componentry, and furthermore secures the placement of components within the lower exterior housing providing resistance to damage caused by shock or movement.

Figure 5A:
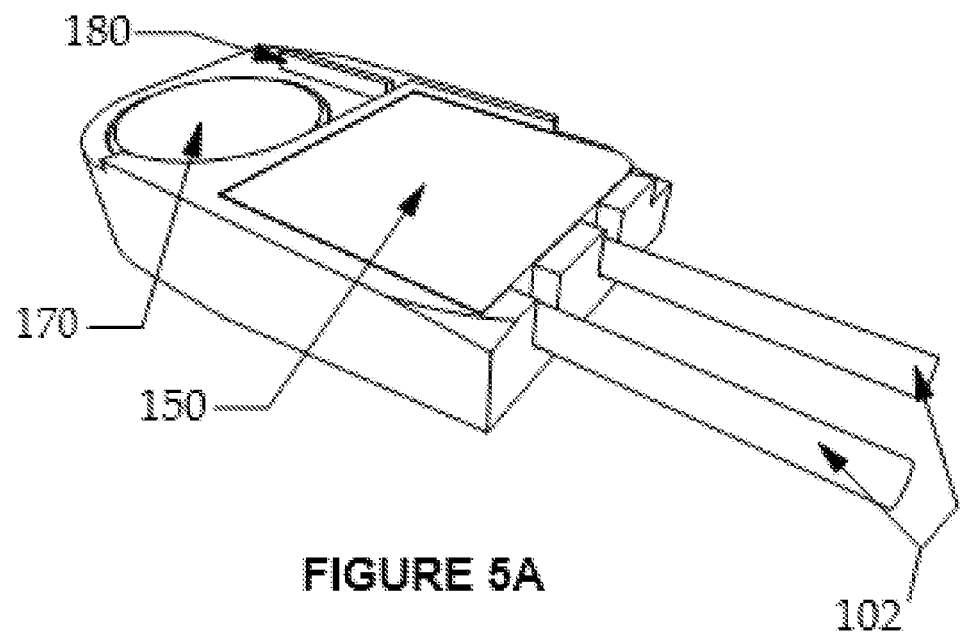
FIGS. 5a and 5b show a top perspective view of the inner chassis housing of an infusion pump of some embodiments housing the infusion pump internal components, with FIG. 5a showing a left perspective view of the chassis and FIG. 5b showing a right perspective view of the chassis.
Figure 5B:
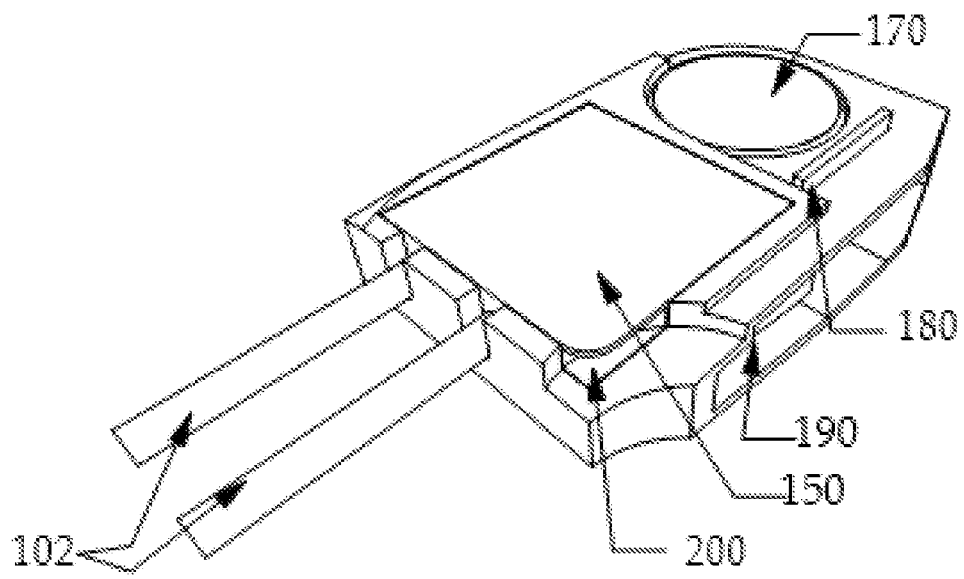

FIG. 5 shows the inner chassis housing the infusion pump componentry. As illustrated in FIGS. 5a and 5b, battery (170) forms a connection with peristaltic pump (150) and on-board computer (190). MicroSD card (180) is pre-programmed with the desired flow rate, volume, duration and fluid characteristics (for example, viscosity and other physical parameters) of the desired infusion treatment, allowing the ready customization of the infusion pump to the prescribed treatment. The microSD card also carries other information, such as minimum and maximum cut-off values to allow for the detection and signaling of malfunctions. The microSD card provides memory for the on-board computer (190) which, in turn, processes the pre-programmed administration regimen. The on-board computer signals the peristaltic pump (150) to activate infusion at a specified flow rate for a specified period.

Figure 6A:
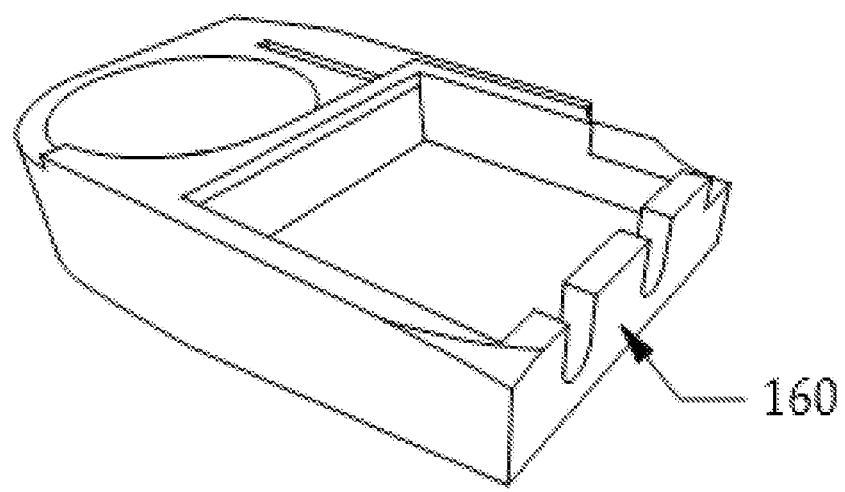
FIGS. 6a and 6b show a top perspective view of the inner chassis housing of an infusion pump of some embodiments, with FIG. 6a showing a left perspective view of the chassis and FIG. 6b showing a right perspective view of the chassis.
Figure 6B:
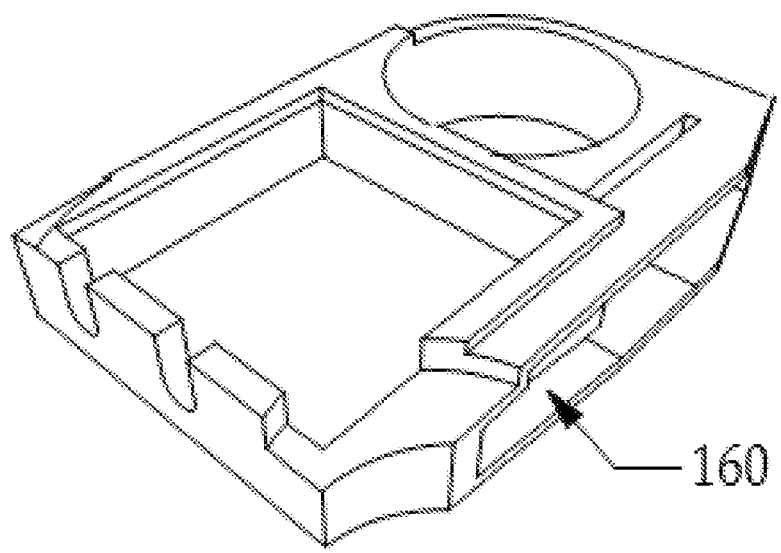

FIG. 6 shows the inner chassis (160) without the infusion pump componentry placed therein. The complete shape and configuration of the inner chassis (160), including channels, grooves and cavities can be clearly seen. FIG. 6a shows the left perspective view and FIG. 6b shows a right perspective view illustrating the cavity housing the on-board computer.

In an alternative embodiment, the lower exterior housing may provide a larger cavity, wherein all infusion pump componentry may be placed therein. In such embodiments, the internal cavity of the lower exterior housing containing the infusion pump componentry and infusion lines to and from the pump may be filled with silicon potting compound (in accordance with the manufacturer's instructions). The hardened potting compound seals and renders water resistant the internal componentry of the infusion pump without the need for additional sealing or assembly of an upper exterior housing. In addition, the hardened potting compound maintains the administration lines in and out of the infusion pump in a fixed, sealed position. The complete unit may be readily sterilized and disposed after use.

Example 2—Disposable Cassette Design

Infusion pumps of some embodiments may be formed in two pieces whereby the two pieces are brought together to provide a complete functional infusion pump device.

Figure 7A:
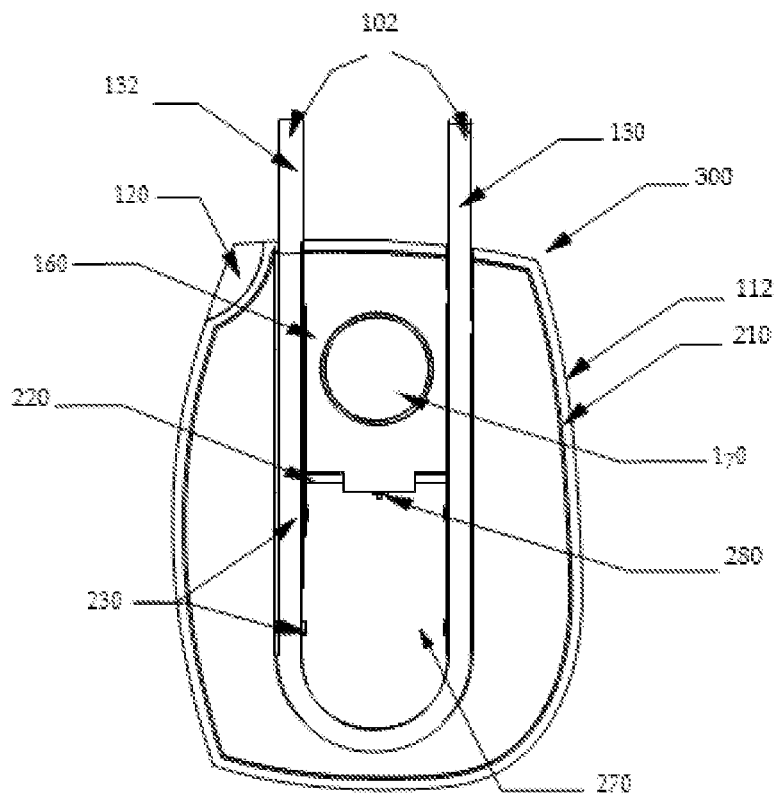
FIGS. 7a and 7b show a plan view of the a two piece infusion pump of some embodiments, with FIG. 7a showing a top plan view of a cassette piece with the exterior housing removed, and FIG. 7b showing a bottom plan view of a pump insert.
Figure 7B:
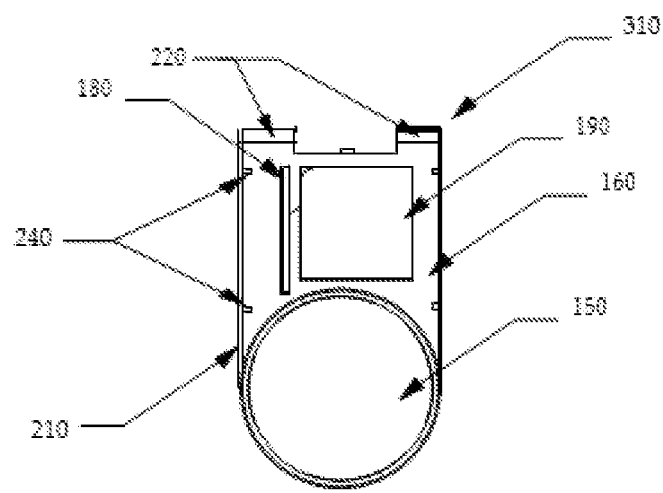

FIGS. 7a and 7b provide a plan view of a two-piece infusion pump of some embodiments including a sterilisable, disposable cassette piece (FIG. 7a) and a reusable, sterilisable (and re-sterilisable) pump insert (FIG. 7b). FIG. 7a shows a top plan view of the cassette piece (300) with the upper exterior housing removed. Infusion lines (102) are set apart with the battery (170) located between infusion line in (130) and infusion line out (132). Infusion lines (102) are placed in a loop to receive the peristaltic pump (150) shown in FIG. 7b. Inner chassis (160), locking clips (220) and groove runners (230) guide the placement of the infusion lines (102) within lower exterior housing (112).

Lower exterior housing (112) is shown as being of identical shape and conformation to the earlier lower exterior housing piece, for realizing economies of scale in small batch manufacture of single piece pumps and two-piece pumps. The lower exterior housing illustrated in FIG. 7a therefore includes a single silicon seal (210) to secure a corresponding upper exterior housing (not shown). An outer case opening point (120) is also provided in the lower exterior housing piece (112) to allow the upper housing piece to be prised open after sealing.

FIG. 7b shows a bottom plan view of the reusable pump insert (310) corresponding to the opening (270) provided in the disposable cassette piece. The pump insert includes on-board computer (190), microSD card (180) and peristaltic pump (150). Components are maintained in position within upper exterior housing (not shown) by inner chassis (160).

The pump insert fits securely within opening (270). Groove runners (230) and grooves (240) provide a tongue and groove mechanism to guide the correct placement the pump insert within the cassette piece. Correct placement of the pump insert ensures that the peristaltic pump cams (not shown) compress the infusion lines to push fluids through the line. Correct placement may also be necessary to ensure that the power connectors (280) at the pump insert and the cassette piece make contact. Once in position, the pump insert is locked in place by a terminal clip in the groove runners (230) and by locking clips (220). The single silicon seal (210) around the perimeter of pump insert housing (290) maintains an impermeable seal between the cassette piece and the pump insert.

Figure 8:
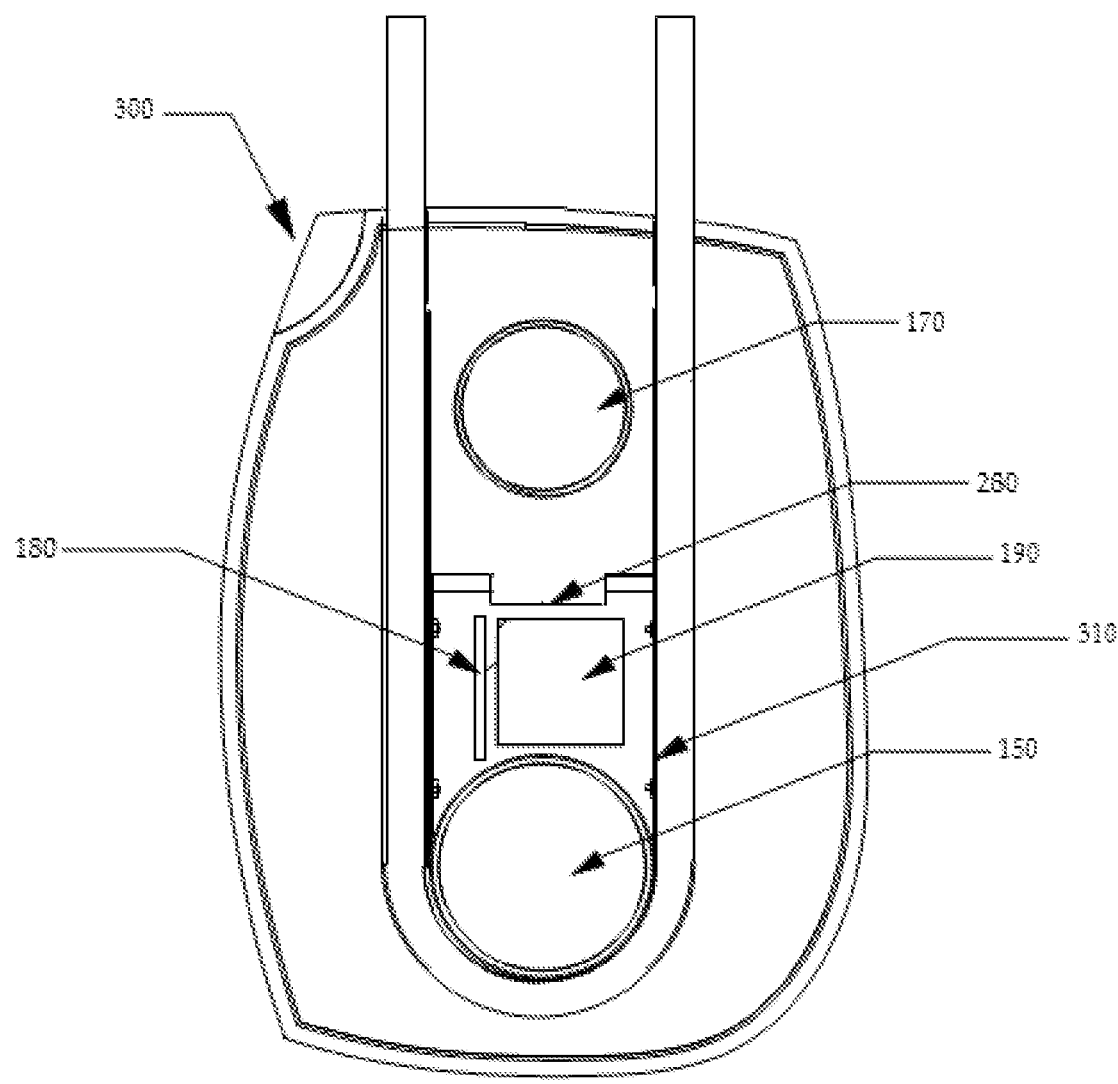
FIG. 8 shows a top perspective view of an assembled two-piece infusion pump of some embodiments showing the pump insert in connection with the cassette piece with the upper exterior housing removed.

FIG. 8 shows a top perspective view of the assembled two-piece infusion pump showing the pump insert (310), with the pump insert housing (290, shown in FIG. 9c) removed, forming a sealed connection with the cassette piece (300); also with the upper exterior housing removed (not shown). Battery (170) forms a connection with the on-board computer (190) and peristaltic pump (150) via power connector (280). Once the pump insert is locked in place and battery (170) is connected, the infusion sequence pre-programmed on microSD card (180) is initiated.

Figure 9A:
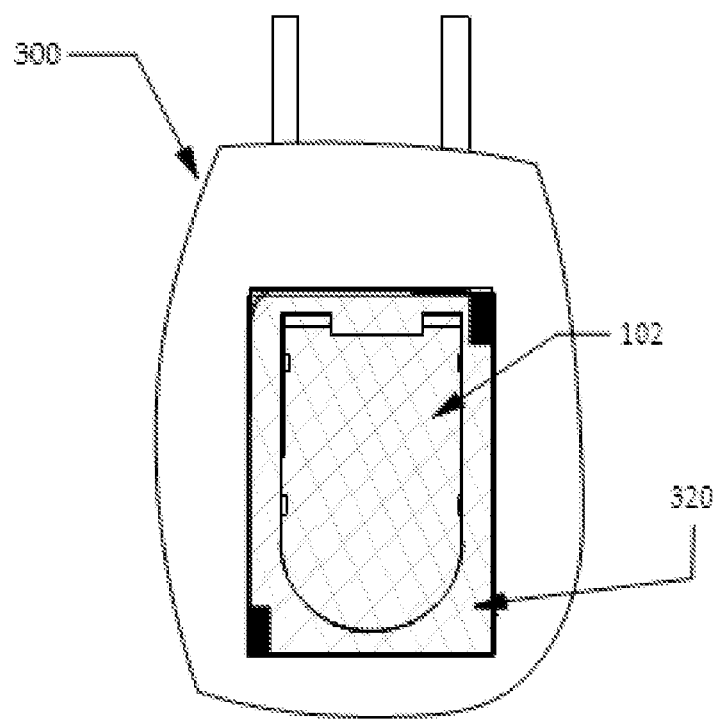
FIGS. 9a, 9b and 9c show a plan view of the a two piece infusion pump of some embodiments, with FIG. 9a showing a top plan view of a cassette piece, FIG. 9b showing a bottom plan view of a pump insert, and FIG. 9c showing a top plan view of a pump insert.
Figure 9B:
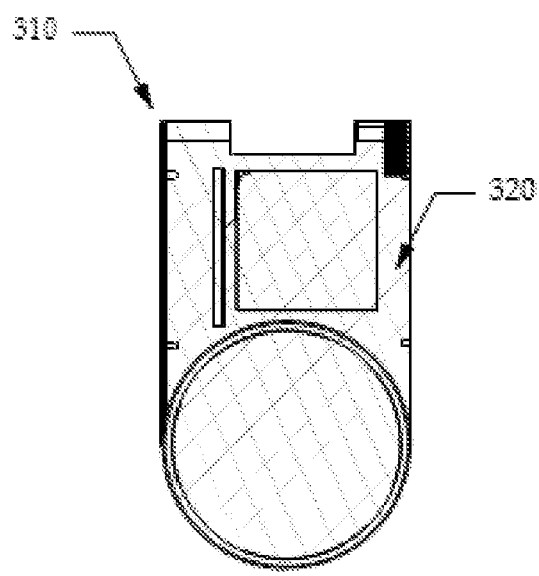
Figure 9C:
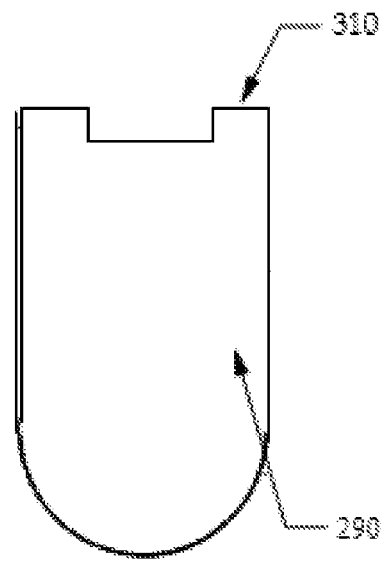

FIGS. 9a, 9b and 9c show a plan view of each piece of the infusion pump with all housing components intact, prepared with a laminated protective coating (320) shown in hatches. FIG. 9a shows a top plan view of the cassette piece with a laminated protective coating (320) covering opening (270). FIG. 9b shows a bottom plan view of the pump insert (310) with a laminated protective coating (320) covering the exposed bottom surface. FIG. 9c shows a top plan view of the pump insert, showing pump insert housing (290). Laminated coating (320) provides additional protection to the internal components of the pump insert (310) and cassette piece (300) and may be sterilized. Immediately prior to use, the laminated coatings (320) on both the cassette piece and the pump insert are removed and both pieces of the pump are brought together, locked and sealed in place.

Figure 10:
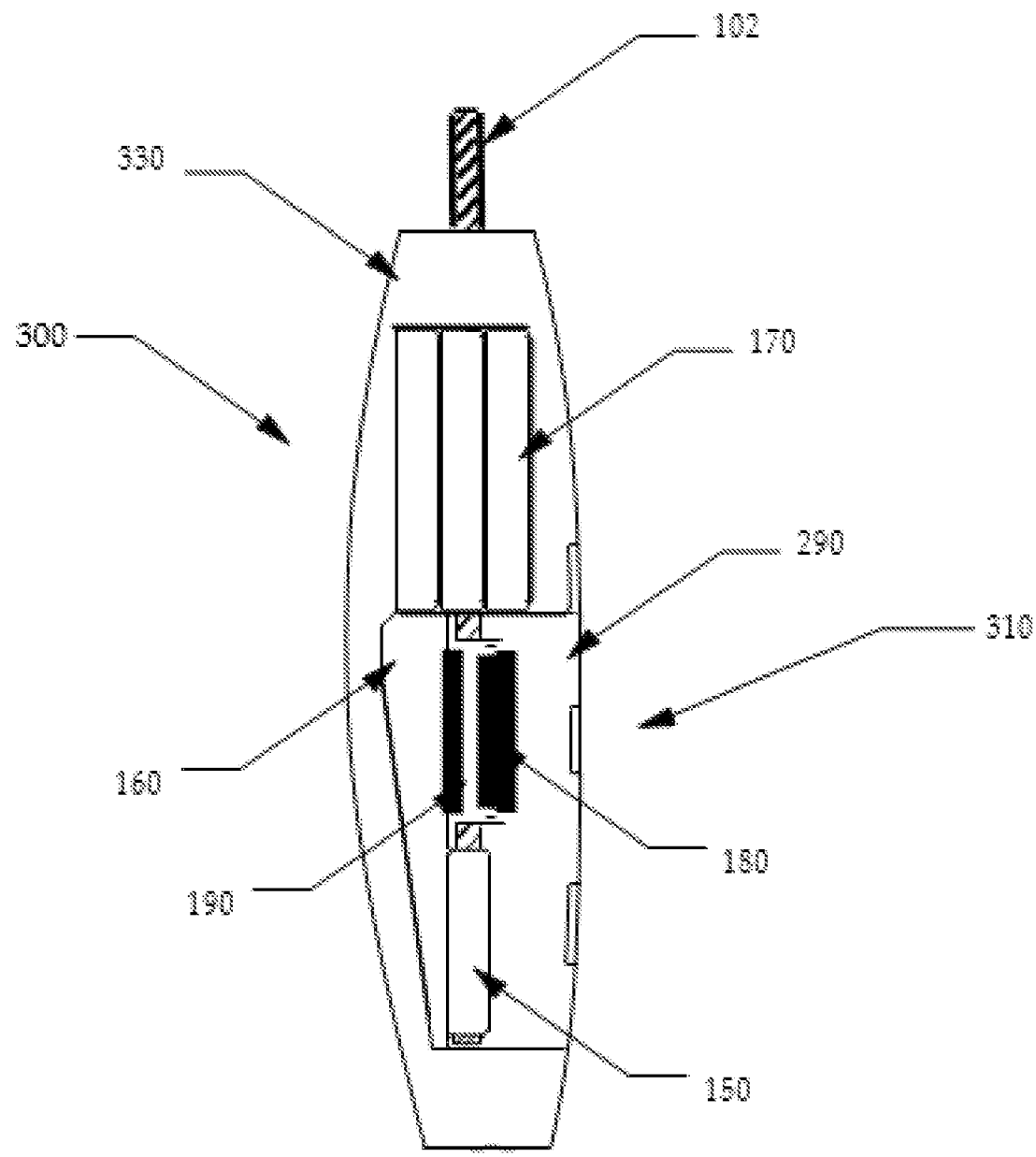
FIG. 10 shows a side sectional view of a two-piece infusion pump of some embodiments with the pump insert in connection with the cassette piece.

FIG. 10 shows a modified embodiment whereby the exterior cassette housing (330) is provided as a single integral piece. FIG. 10 shows a side sectional view of a two-piece infusion pump with the pump insert (310) in connection with the cassette piece (300). Components of the cassette piece are shown, including exterior cassette housing (330), battery (170), inner chassis (160) and infusion lines (102) shown in hatched lines. Components of the pump insert are shown including pump insert housing (290), microSD card (180), on-bard computer (190) and peristaltic pump (150). Once locked in place, the pump insert and cassette piece form a smooth, uniform exterior to the infusion pump.

While both the cassette piece and pump insert are sterilisable, the pump is provided in two portions to provide the option of re-sterilizing or simply reusing the pump insert, while the cassette piece may be replaced together with the patent's administration set.

As described above in relation to Example 1, it is anticipated that the inner chassis provided in the two-piece infusion pump may be readily substituted for a suitable silicon potting material in accordance with the methods provided above.

Example 3—Infusion Pump Use

Operative Tolerances

During operation, the infusion pump flow rate will be pre-programmed at a set specific flow rate. For the majority of indications, the set flow rate will be between 1.5 ml/hour and 10 ml/hour. The infusion pump also includes a "keep line open" function. When the infusion program is complete, the pump continues with a flow rate of the lower programmed flow rate or 0.5 ml/hr for 4 hours.

The infusion pump will continue to infuse at the set rate until the infusion fluid is depleted. The pump will detect that there is no fluid available to infuse and initiate a termination sequence. Alternatively, the pump will sense that the lower threshold fluid volume level is no longer met and/or that the calculated infusion period has elapsed and will initiate a termination sequence.

The infusion pump infuses continuously at the set rate provided that an average flow rate at the pre-set rate over a five-minute period is achieved. In addition, the flow rate must or should fall within a tolerance level of at least +/−6% of the set flow rate. However, for some indications the tolerance level may be set as low as +/−2% of the set flow rate.

The flow rate must or should fall within the desired tolerance level at atmospheric pressures ranging from 695 to 1000 hPa, at ambient temperatures ranging from −10° C. to +40° C., at atmospheric relative humidity ranges of between 10% to 90% non-condensing, and for medication temperatures from +2° C. to +22° C. The infusion pump is also suitable for storage at temperatures of up to +70° C.

The infusion pump adapts to the administration of fluid of a wide range of viscosities. An adjusted flow rate may either be calculated on pre-set values of fluid viscosity, or a sensed viscosity may trigger a flow rate adjustment in real time. Flow rate adjustments are made for viscosities ranging from 0.7 mm$^2$/s-1.7 mm$^2$/s.

The maximum pumping pressure must or should be set at 1200 mmHg. A backflow prevention device is also included in the system, effective to a pressure of up to 1200 mmHg. At maximum pressure and flow rate the pump will only emit a noise level less than 40 dB (A) at 0.5 m.

Malfunction Protection

When a maximum threshold flow rate is breached a malfunction sequence is initiated, involving the termination of the pump and/or motor mechanism and signaling of the alarm mechanism, to ensure the patient is not subjected to an overdose. This safety feature offers protection in the event of a pump malfunction.

An occlusion malfunction sequence is initiated in response to an upstream or downstream occlusion event. When line pressure is detected as reaching the threshold of 825 mmHg (160 kPa)+/−375 mmHg16 (50 kPa), the pump commences pause mode and stops pumping. The event also initiates an alarm (not audible). The pump will resume the pre-set infusion regimen once the occlusion is removed.

Administration sets suitable for use with the infusion pump include an in-line filter and venting system to remove the passage of particulates or air passing to the patient.

Suitable administration sets must or should also include an infusion line clamp for the manual cessation of infusion as an additional safety feature in the event of a pump or motor malfunction.

Physical Features

The infusion pump includes an activation mechanism and an indication light located beneath the outer housing, which indicates the operational status of the infusion pump. A green static light indicates the operational status of the infusion pump and changes color to red during a malfunction or termination sequence. The infusion pump does not include an externally programmable programming interface. The infusion sequence is pre-programmed on an internal microSD card which cannot be amended once the pump has been assembled and sterilized.

The infusion tubing terminates in a luer-lock connection for connection with a variety of infusion bags and vascular access devices (VADs) (midline, central, intrathecal etc.).

The infusion pump allows for extended infusions without need to change batteries; between 24 hours at 10 ml/hour and 48 hours at 10 ml/hour.

Throughout this specification the word "include", or variations such as "includes" or "including", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for some embodiments. It is not to be taken as an admission that any or all of these matters form part of the related art base or were common general knowledge in the field relevant to some embodiments as it existed in Australia or elsewhere before the priority date of each claim of this application.

While the presently disclosed subject matter has been described above in terms of specific embodiments, it is to be understood that the presently disclosed subject matter is not limited to these disclosed embodiments. Upon reading the teachings of this disclosure many modifications and other embodiments of the presently disclosed subject matter will come to the mind of those of ordinary skill in the art to which the presently disclosed subject matter pertains, and which are intended to be and are covered by both this disclosure and the appended claims.

It is indeed intended that the scope of some embodiments should be determined by proper interpretation and construction of the appended claims and their legal equivalents, as understood by those of ordinary skill in the art relying upon the disclosure in this specification and the attached figures.

REFERENCES

United States Food and Drug Administration (2010) *White Paper: Infusion Pump Improvement Initiative*; http://www.fda.gov/medicaldevices/productsandmedicalprocedures/GeneralHospitalDevicesandSupplies/InfusionPumps/ucm205424.htm#types.

National Patient Safety Agency (2004) *Safer practice notice*; Issue 1; 20 May 2004.

Mizuuchi, M. and A. Namiki (2003) *The infusion rate of most disposable, non-electric infusion pumps decrease under hypobaric conditions*, Can J Anesth 7 (50).

Grissinger, M. (2013) *Improved Safety Needed in Handling Elastomeric Reservoir Balls Used for Pain Relief*, Medication Errors, Vol. 38 No. 5, May 2013.

Irish Medicines Board (2008) *Disposable Infusion Devices IMB Safety Notice: SN2008(06)* Medical Device Safety Notice.

Ganapathy, S. Amendola, A. Lichfield, R. Fowler, P. J. and Ling, E. (2000) *Elastomeric pumps for ambulatory patient controlled regional analgesia*, Can J Anesth, 47 (9).

Thornton, P. (2015) *Medication Safety*, Journal of Pharmacy Practice and Research, 45, 450-458.

Institute for Safe Medication Practices Canada (2015) *Selection of Incorrect Medication Pump Leads to Chemotherapy Overdose*, ISMP Canada Safety Bulletin, 15 (7).

What is claimed is:

1. A non-implantable portable device for transferring fluids from an external vessel via an administration set and controllably infusing the fluids into a patient, the portable device comprising:

a protective housing including a first protective housing piece that includes a first wall defining an infusion line aperture that extends through the first wall, the protective housing defining an internal cavity that is contiguous with the infusion line aperture;

infusion tubing configured to allow the fluids to pass therethrough, the infusion tubing including a first portion and a second portion, the first portion and the second portion extending through the first wall, the first portion being disposed within the infusion line aperture, the first portion including an infusion line in configured to engage the external vessel for transporting fluids from the external vessel, the second portion including an infusion line out configured to engage with a patient's vascular access device for transporting fluids to the patient;

a seal disposed at the protective housing and configured to substantially isolate the internal cavity from an exterior of the protective housing;

a pump disposed within the internal cavity;

a power source disposed within the internal cavity that provides power to the pump;

an on-board computer for controlling the pump to draw the fluids through the infusion line in and/or the infusion line out at a preset flow rate, the on-board computer being disposed within the internal cavity of the protective housing; and a computer programming interface configured for receiving instructions for the preset flow rate at which the on-board computer controls the pump, the computer programming interface being entirely disposed within the internal cavity as to be inaccessible from the exterior of the protective housing to thereby impede manually re-programming the preset flow rate.

2. The non-implantable portable device of claim 1, further including an occlusion sensor and a pump actuator that are substantially disposed within the internal cavity.

3. The non-implantable portable device of claim 2, wherein the on-board computer includes a processor, and the computer programming interface is configured to receive instructions from a user for modulating the activity of the pump actuator.

4. The non-implantable portable device of claim 1, wherein the computer programming interface comprises a memory device reader.

5. The non-implantable portable device of claim 1, wherein the computer programming interface comprises a removable memory device reader, is configured to impede editing subsequent to installation within the internal cavity, and is configured to receive a pre-programmed memory device.

6. The non-implantable portable device of claim 1, wherein the computer programming interface comprises a wireless signal receiver, and is configured to impede editing subsequent to installation within the internal cavity.

7. The non-implantable portable device of claim 1, wherein the protective housing includes a second protective housing piece that includes a second wall and the seal formed between the first wall and the second wall, and configured to substantially isolate the internal cavity from an exterior of the protective housing so as to impede access to the pump from the exterior of the protective housing, the computer programming interface being disposed within the sealed internal cavity so as to be inaccessible from the exterior of the protective housing to thereby impede manually re-programming the preset flow rate.

8. The non-implantable portable device of claim 7, wherein the non-implantable portable device is configured to be wearable by a user and the first protective housing piece and second protective housing piece are formed from a substantially impervious, firm material capable of providing shock absorption.

9. The non-implantable portable device of claim 1, wherein the computer programming interface and the on-board computer comprises a memory device reader, is configured to impede editing subsequent to installation within the internal cavity, and is configured to receive a pre-programmed memory device.

10. The non-implantable portable device of claim 9, wherein the first wall or a second wall of the protective housing is configured to receive the memory device reader therethrough.

11. The non-implantable portable device of claim 1, wherein the pump further includes an occlusion sensor and a pump actuator, and the computer programming interface is configured to receive instructions from a user for modulating the activity of the pump actuator.

12. The non-implantable portable device of claim 11, wherein the on-board computer is a memory device reader, the on-board computer being operated by software configured to impede editing subsequent to installation of the on-board computer within the protective housing, the on-board computer being configured to receive a pre-programmed memory device, and the protective housing being configured to receive the pre-programmed memory device there through.

13. A method of manufacturing the non-implantable portable device according to claim 7, comprising:
placing the pump within the internal cavity defined by the protective housing; and
deploying the seal to engage the second protective housing piece with the first protective housing piece to secure the pump within the internal cavity of the protective housing.

14. A method of manufacturing the non-implantable portable device according to claim 1, comprising:
placing the pump and the on-board computer within the internal cavity of the protective housing;
placing a part of the infusion tubing within the infusion line aperture; and
deploying the seal to secure the pump and the on-board computer within the internal cavity of the protective housing.

15. A method of controllably infusing fluids into a patient, comprising:
obtaining the non-implantable portable device according to claim 1,
obtaining the fluids contained within the external vessel;
connecting a vascular access device to the patient;
connecting a vascular access device fitting to a terminal end of the infusion line out;
connecting the infusion line in to the external vessel;
connecting the infusion line out to the patient;
priming the infusion tubing; and
activating the non-implantable portable device.

16. A non-implantable portable device for transferring fluids from an external vessel via an administration set and controllably infusing the fluids into a patient, the portable device comprising:
a protective housing including a first protective housing piece that includes a first wall defining infusion line apertures that extend through the first wall, the protective housing defining an internal cavity that is contiguous with the infusion line apertures;
infusion tubing configured to allow the fluids to pass therethrough, the infusion tubing including a first portion and a second portion, the infusion line apertures being configured to allow the first portion and the second portion to extend through the first wall, the first portion including an infusion line in configured to engage the external vessel for transporting fluids from the external vessel, the second portion including an infusion line out configured to engage with a patient's vascular access device for transporting fluids to the patient;

a seal disposed at the protective housing and configured to substantially isolate the internal cavity from an exterior of the protective housing;

a pump disposed within the internal cavity;

a power source disposed within the internal cavity that provides power to the pump;

an on-board computer for controlling the pump to draw the fluids through the infusion line in and/or the infusion line out at a preset flow rate, the on-board computer being disposed within the internal cavity of the protective housing; and a computer programming interface configured for receiving instructions for the preset flow rate at which the on-board computer controls the pump, the computer programming interface being entirely disposed within the internal cavity as to be inaccessible from the exterior of the protective housing to thereby impede manually re-programming the preset flow rate.

* * * * *